United States Patent [19]

Mitzlaff et al.

[11] 4,234,484
[45] Nov. 18, 1980

[54] PROCESS FOR THE PREPARATION OF CYCLIC ENAMIDES

[75] Inventors: Michael Mitzlaff, Bad Homburg; Klaus Warning, Liederbach, both of Fed. Rep. of Germany

[73] Assignee: Hoechst Aktiengesellschaft, Frankfurt am Main, Fed. Rep. of Germany

[21] Appl. No.: 899,783

[22] Filed: Apr. 25, 1978

[30] Foreign Application Priority Data

Apr. 27, 1977 [DE] Fed. Rep. of Germany ....... 2718666

[51] Int. Cl.$^3$ ...................... C07B 3/00; C07D 202/20; C07D 207/27; C07D 223/04
[52] U.S. Cl. ...................... 260/239 BE; 260/239.3 A; 260/326.4; 260/326.5 E; 260/326.5 FL; 546/249; 546/252; 546/290
[58] Field of Search .................. 260/239 BE, 326.5 E, 260/297 R, 326.4, 313.1, 239.3 A, 295 R, 326.5 FL; 204/78; 546/249, 252, 290

[56] References Cited
PUBLICATIONS

Nyberg et al, Acta Chemica Scandinavica, B, vol. 30, pp. 640–642, (1976).
Nyberg, Synthesis, 1976, pp. 545–546.

Primary Examiner—Alton D. Rollins
Attorney, Agent, or Firm—Curtis, Morris & Safford

[57] ABSTRACT

Special cyclic enamides are prepared by splitting off alcohols catalytically from the corresponding alkoxylated cyclic amides, in the presence of at least one tetraalkylammonium and/or alkali metal salt of tetrafluoroboric acid and/or of hexafluorophosphoric acid as the catalyst, at a temperature of from about 120° to 250° C., distilling off the detached alcohol and isolating the formed enamide in known manner. Particularly preferred starting compounds are those cyclic amides which have been obtained by anodic alkoxylation of corresponding cyclic N-compounds in an alcohol in the presence of supporting electrolytes which are identical with the catalysts subsequently used for splitting off the alcohol, and by distilling off the alcohol from the reaction batch. The enamides are valuable starting products and intermediates for various syntheses, for example, syntheses of prostaglandins and of other pharmaceuticals.

18 Claims, No Drawings

PROCESS FOR THE PREPARATION OF CYCLIC ENAMIDES

Enamides are known intermediates for chemical reactions, for example for the synthesis of heterocyclic compounds and peptides (cf. for example J. Szmuszkovicz, "Enamines" in R. A. Raphael et al., Advances in Organic Chemistry, Methods and Results, Interscience Publishers, New York (1963), 1–113; A. G. Cook ed., Enamines: Synthesis, Structure and Reactions, Marcel Dekker, New York and London (1969).

In particular, cyclic enamines and enamides have been used successfully in the synthesis of alkaloids (cf. E. Wenkert. Acc. Chem. Res. 1 (1968) 78; E. Wenkert et al., J. Org. Chem. 33 (1968) 747–51; N. J. Nelson and F. P. Hauck, Jr., J. Am. Soc. 79 (1957) 5279–92; German Patent Application No. P 26 36 098.5; O. Cervinka in A. G. Cook, Enamides, page 253 and following pages).

A number of preparation processes for enamines are already known:

The cyclization of unsaturated amines in the form:

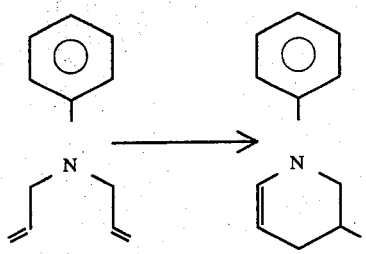

in the presence of a basic catalyst yields 1,2,3,4-tetrahydropyridine (cf. patent of German Democratic Republic No. 113,226). This process, however, is limited to six-membered ring enamines.

The reaction of N-methyllactams with Grignard reagents

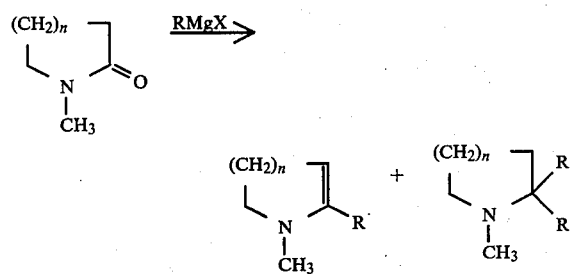

gives a mixture of enamines and a 2,2-dialkylamine, only if n is 1 or 2. This process, certainly, is a means to obtain five-membered and six-membered ring enamines. However, these enamines are always obtained in admixture with dialkylamine, which is difficult to separate sometimes even, its separation does not succeed. (Cf. O. Cervinka, loc. cit., page 257).

Enamines may further be prepared by dehydrogenation of alkyl-substituted cyclic amines using mercury acetate (cf., for example, J. Am. Chem. Soc. 79 (1957) 5279–92), this method being only employable on a laboratory scale.

According to a further method (cf. Synthesis (1976) 545–6) alcohol may be split off catalytically from cyclic 1-formyl-2-methoxyamines and thus enamides are obtained:

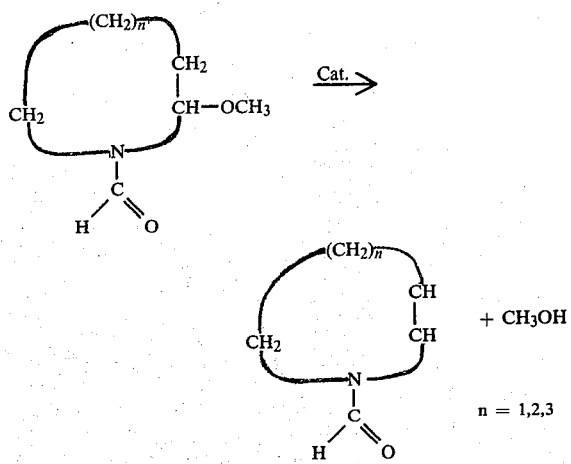

In this method ammonium bromide is exclusively used as the catalyst, since acids such as formic acid, trifluoroacetic acid or sulfuric acid, certainly, bring about a splitting off of methanol, but also catalyze the polymerization of the formed enamides during the working up, even when present in small traces. The splitting off temperatures employed are in the range of from 140° to 205° C. and the yields are in the range of from about 70 to 90% of the theory.

The cyclic 1-formyl-2-methoxyamines, which are required as starting compounds in the above process, are prepared by electrolysis of a methanolic solution of cyclic formamides in the presence of tetrabutylammonium tetrafluoroborate $(C_4H_9)_4NBF_4$ as the supporting electrolyte (cf. Acta. Chem. Scand. Ser. B 30 (1976) 640–2).

This process comprising an electrolysis and a subsequent catalytic detachment of methanol furnishes the corresponding 1-formylenamines in rather elegant manner and in a good yield from cyclic 1-formylamines. It has, however, the disadvantage that two different salts, namely tetrabutylammonium tetrafluoroborate in the electrolysis and ammonium bromide in the splitting off of methanol, must be used as the supporting electrolyte or as the catalyst, respectively, in both steps, as a consequence of which the methoxylated formylamine must be isolated.

It is therefore an object of the present invention to develop an improved and simplified process for the preparation of cyclic enamides.

This object is achieved by using tetraalkylammonium tetrafluoroborates and alkali metal tetrafluoroborates as well as alkali metal hexafluorophosphates, which are efficient both as the supporting electrolyte in the electrolysis and as the catalyst in the subsequent splitting off of alcohol from the alkoxy compounds formed during electrolysis.

The present invention, consequently, provides a process for the preparation of cyclic enamides of the formula:

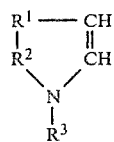  (I)

in which $R^1$ is a single bond or an optionally branched, preferably linear, alkylene group with 1 to 8 carbon atoms,

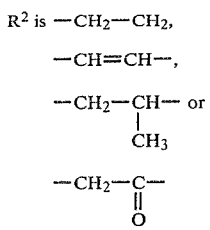

in which the carbon atom carrying the $CH_3$ or the oxygen radical is bound to the ring nitrogen atom, $R_3$ is a hydrogen atom, a secondary or tertiary $(C_3-C_4)$alkyl group,

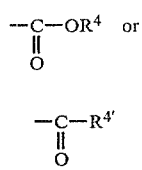

in which $R^4$ is a $(C_1-C_6)$alkyl group, a $(C_6-C_{10})$aryl or a $(C_7-C_{10})$aralkyl group optionally carrying inert substituents, preferably 1 or 2, such as $(C_1-C_4)$alkyl radicals, preferably $CH_3$; F, Cl, Br and others, $R_4$ preferably being $CH_3$, $C_2H_5$ or the abovementioned substituent $C_6H_5$ or $C_6H_5CH_2$ group, $R^{4'}$ has the same meaning as $R_4$ and additionally is H, provided that only one of the radicals $R^2$ and $R^3$ contains

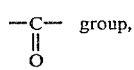 group, by catalytic splitting off of alcohols from cyclic amides at an elevated temperature, which comprises heating cyclic amides of the formula

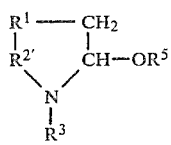  (II)

in which $R^1$ and $R^3$ have the meaning given in formula I,

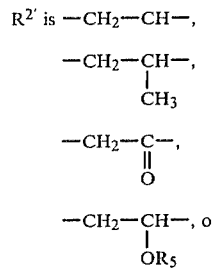

the carbon atoms carrying the $CH_3—$, $O—$ or the $OR_5—$ radical being bound to the ring nitrogen atom and $R_5$ is a primary or secondary $(C_1-C_4)$alkyl group, preferably the $CH_3$ group, provided that only one of the radicals $R^{2'}$ and $R^3$ contains a

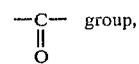 group, to a temperature of from about 100° to 250° C., in the presence of at least one tetraalkylammonium and/or alkali metal salt of tetrafluoroboric acid and/or of hexafluorophosphoric acid as the catalyst, distilling off the detached alcohol $R^5OH$, preferably under reduced pressure, and isolating the formed enamide of the formula I in known manner, preferably by distillation under reduced pressure.

Preferred starting compounds in the process of the present invention are those cyclic amides of the formula II which have been obtained by anodic alkoxylation of cyclic nitrogen compounds of the formula III

  (III)

in which $R^1$ and $R^3$ have the same meaning as in the formulae I and II and

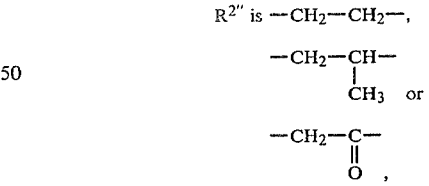

the carbon atom carrying the $CH_3$ or the oxygen radical being bound to the ring nitrogen atom and only one of the radicals $R^{2''}$ and $R_3$ containing a C(O) group, in an alcohol $R^5OH$, in which $R^5$ has the same meaning as in the formula II, in the presence of supporting electrolylytes, which are identical with the catalysts, employed subsequently for detaching the alcohols, namely tetraalkylammoium and alkali metal tetrafluoroborates and alkali metal hexafluorophosphates, and by distillation of the alcohol $R^5OH$ from the reaction batch. The anodic alkoxylation proceeds according to the prescription of Belgian Pat. No. 845,901, both when employing cyclic 1-acylammines and lactams.

Examples of compounds of the formula III are:

1-formylpyrrolidine, 1-acetylpyrrolidine, 1-butyrylpyrrolidine, 1-benzoylpyrrolidine, 1-formylpiperidine, 1-acetylpyrrolidine, 1-acetyl-2-methylpiperidine, 1-acetyl-4-methylpiperidine, 1-butyrylpiperidine, 1-benzoylpiperidine, 1-benzoyl-2-methylpiperidine, 1-(2'-fluorobenzyl)-piperidine, 1-(2'-chlorobenzoyl)-piperidine, 1-(3'-methylbenzoyl)-piperidine, 1-(2',4'-dichlorobenzoyl)-piperidine, 1-(3'-trifluoromethylbenzoyl)-piperidine, 1-formylhexahydroazepine, 1-acetylhexahydroazepine, 1-butyrylhexahydroazepine, 1-benzoylhexahydroazepine, piperidone-(2), 1-propylpiperidone-(2), ε-caprolactam, caprylolactam and laurinolactam, N-methoxycarbonylpyrrolidine, N-ethoxycarbonylpyrrolidine, N-n-propoxycarbonylpyrrolidine, N-n-butoxycarbonylpyrrolidine, N-i-butoxycarbonylpyrrolidine, N-phenoxycarbonylpyrrolidine, N-benzyloxycarbonylpyrrolidine, N-methoxycarbonylpiperidine, N-ethoxycarbonylpiperidine, N-i-propoxycarbonylpiperidine, N-n-butoxycarbonylpiperidine, N-phenoxycarbonylpiperidine, N-benzoyloxycarbonylpiperidine, N-methoxycarbonylhexahydroazepine, N-ethoxycarbonylhexahydroazepine, N-butoxycarbonylhexahydroazepine, N-phenoxycarbonylhexahydroazepine, N-benzylcarbonylhexahydroazepine, etc.

Examples of compounds of the formula II obtainable by anodic alkoxylation from compounds of the formula III are:

1-formyl-2-ethoxypyrrolidine, 1-formyl-2-n-butoxypyrrolidine, 1-formyl-2,5-diethoxypyrrolidine, 1-acetyl-2-ethoxypyrrolidine, 1-acetyl-2-n-butoxypyrrolidine, 1-formyl-2,4-dimethyl-6-n-propoxy-piperidine, 1-butyryl-2-methoxypiperidine, 1-butyryl-2-ethoxypiperidine, 1-acetyl-2-methoxy-4-methylpiperidine, 1-acetyl-2,6-dimethoxy-4-methylpiperidine, 1-benzoyl-2-n-butoxypiperidine, 1-(2',4'-dichloro-benzoyl)-2-methoxypiperidine, 1-formyl-2-ethoxyhexahydroazepine, 1-formyl-2,7-diethoxy-hexahydroazepine, 1-acetyl-2-n-butoxy-hexahydroazepine, 1-methoxycarbonyl-2-methoxypyrrolidine, 1-methoxycarbonyl-2,5-dimethoxypyrrolidine, 1-methoxycarbonyl-2-ethoxypyrrolidine, 1-methoxycarbonyl-2-n-butoxypyrrolidine, 1-phenoxycarbonyl-2-methoxypyrrolidine, 1-phenoxycarbonyl-2-ethoxypyrrolidine, 1-benzyloxycarbonyl-2-methoxypyrrolidine, 1-phenoxycarbonyl-2-ethoxypiperidine, 1-methoxycarbonyl-2-methoxypiperidine, 1-benzyloxycarbonyl-2-ethoxypiperidine, 1-isopropyl-6-methoxypiperidone-(2), 1-isopropyl-6-ethoxypiperidone-(2), 4-methyl-6-ethoxy-piperidone-(2), 7-ethoxycaprolactam.

Since compounds of the formula I having five ring members are obtained only intermediately according to the process of the invention, if R² is —CH₂—C(O) in formula II, these compounds being lactams, and since these compounds of the formula I rapidly rearrange under cleavage conditions to form the isomeric 3,4-unsaturated enamides, R¹ of lactams preferably should contain of from 1 to 8 carbon atoms. In the rest of the compounds II R₁ preferably is a single bond or an alkylene group having of from 1 to 3 carbon atoms.

Preferred starting compounds for the process of the invention, consequently, are those cyclic amides of the formula II, in which, if R²' is

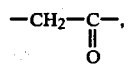

R₁ is an optionally branched, but preferably linear alkylene group with 1 to 8 carbon atoms and, if

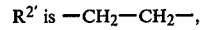

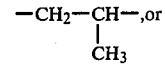

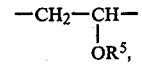

R¹ is a single bond or a branched or linear alkylene group with 1 to 3 carbon atoms.

Suitable catalysts for the process of the invention are tetra-(C₁-C₄)alkylammonium salts and the Li, Na, K, Rb and/or Cs salts of tetrafluoroboric acid and/or of hexafluorophosphoric acid, in particular the sodium and/or potassium salts. Mixtures of these salts may also be used naturally. The same salts are also used for the anodic alkoxylation of the compounds III.

The amount of these catalysts is in the range of from about 0.01 to 60% by weight or more, calculated on the compound of the formula II, preferably in the range of from about 0.1 to 20% by weight. The upper limit is not critical and is advisable only for economical reasons.

The process of the present invention is generally carried out in the following manner: The compound II and the catalyst are mixed homogeneously, optionally in the presence of a solvent or dispersion agent, which is distilled off subsequently, the batch is heated to the reaction temperature and heating is continued until the alcohol R⁵OH is no longer distilled off, optionally even under slightly reduced pressure, and the formed enamide of the formula I distills over under reduced pressure and at a temperature which preferably should not surpass the reaction temperature. Depending on the nature of the compound II employed, either 1 or 2 mols of alcohol R⁵OH are liberated.

The process according to the invention enables a great number of cyclic enamides of the formula I to be prepared in excellent yields from the corresponding alkoxy compounds of the formula II using simple and very specific catalysts. The advantage of the process of the invention becomes particularly evident, when preparing the starting compounds II with the use of supporting electrolytes which are identical with the catalysts employed for splitting off alcohols from the compounds of the formula II. Upon completion of the alkoxylation of the compounds III, only the alcohol R⁵OH need be distilled from the reaction batch and the distillation residue need be heated. The desired enamide I is immediately obtained during this process. It was, certainly, known to use a tetraalkylammonium tetrafluoroborate [(C₃H₉)₄NBF₄, Acta Chem. Scand. Ser. B 30 (1976), 640-2] and furthermore alkali metal tetrafluoroborate and alkali metal hexafluorophosphates (cf. German Offenlegungsschrift No. 21 13 338) as supporting electrolytes for the anodic alkoxylation of N-acyl compounds covered by the formula III; however, it was not known to use these salts (and the tetraalkylammonium hexafluorophosphates) for splitting off alcohols from the compounds of the formula II to obtain cyclic enamides I. The catalytic effect of the salts, which are used according to the invention and act highly specifically and selectively was surprising and not to be expected. Owing to this action, these salts, which are known as conducting salts for a number of anodic alkoxylations, may be employed in a completely different function as catalysts for splitting off alcohols from the alkoxylated compounds. The alkali metal salts have the advantage over the tetraalkylammonium salts of being more readily obtainable and less expensive compounds. In comparison thereto, the catalytically acting ammonium bromide which is known from the state of the art for splitting off methanol from 1-formyl-2-methoxyamines, is not appropriate as a supporting electrolyte for the preparation of alkoxy compounds of the formula II in an electrochemical way, as tests of the applicants have shown.

The enamides of the formula I prepared according to the invention are valuable starting products and intermediates for various syntheses, for example syntheses of prostaglandins and of other pharmaceuticals. The enamides having five or four carbon atoms in the ring and a formyl or acetyl group at the ring nitrogen atom may be converted, in particular according to the process of German patent application No. P 26 36 098.5, into the corresponding tripiperideines or tripyrrolines in simple and elegant manner by saponification in aqueous and/or alcoholic solution in the presence of strong acids or bases and trimerization at a pH of at least 8. The tripiperideines and tripyrrolines are interesting compounds for the syntheses of pharmaceuticals, alkaloids and so on.

The following examples illustrate the invention:

(A) EXAMPLES 1 to 13

Catalytic splitting off of alcohol from cyclic alkoxyamides according to the invention:

EXAMPLE 1

41.0 g of 1-acetyl-2-methoxypiperidine in the presence of 0.5 g of sodium tetrafluoroborate in an oil bath are slowly heated to 130° C., under normal pressure, in a 100 ml glass flask provided with a Vigreux column and a Liebig condenser, whereupon methanol distills over. Thereafter the pressure is slowly lowered, until the reaction product, too, distills over and is collected in the receptacle.

30.3 g of 1-acetyl-1,2,3,4-tetrahydropyridine are obtained which correspond to a yield of 92.8%.

EXAMPLES 2 to 13

Details of these examples carried out on principle in analogous manner to Example 1 can be seen from table 1.

Table 1

| Example | Starting material (N,O-acetal) | [g] | catalyst | [g] | highest temp. in the flask [°C.] | final product (cycl.-enamide) | [g] | material yield |
|---|---|---|---|---|---|---|---|---|
| 2 | 1-acetyl-2-methyl 6-methoxy-piperidine | 51.5 | KPF$_6$ | 0.5 | 148 | 1-acetyl-2-methyl-1,2,3,4-tetrahydropyridine | 38.0 | 90.7 |
| 3 | 1-formyl-2-methoxy piperidine | 28.6 | NaBF$_4$ | 0.24 | 150 | 1-formyl-1,2,3,4-tetrahydropyridine | 21.2 | 95.4 |
| 4 | 1-benzoyl-2-methoxy-piperidine | 43.8 | KPF$_6$ | 0.6 | 140 | 1-benzoyl-1,2,3,4-tetrahydropyridine | 36.7 | 98.0 |
| 5 | 1-acetyl-2-methoxy-hexahydro-azepine | 34.2 | NaBF$_4$ | 0.1 | 170 | 1-acetyl-1-H-2,3,4,5-tetrahydroazepine | 21.2 | 76.2 |
| 6 | 1-(2'-fluoro-benzoyl)-2-methoxypiperidine | 17.2 | NaBF$_4$ | 0.08 | 145 | 1-(2'-fluoro-benzoyl)-1,2-3,4-tetrahydropyridine | 13.5 | 90.9 |
| 7 | 1-(3'-methylbenzoyl)-2-methoxy-piperidine | 32.2 | NaBF$_4$ | 0.15 | 150 | 1-(3'-methylbenzoyl)-1,2,3,4-tetrahydropyridine | 25.0 | 90.0 |
| 8 | ε-methoxy-ε-caprolactam | 14.3 | NaBF$_4$ | 0.1 | 160 | 1-H-2,3-4,5-tetrahydroazepine-2-one | 8.1 | 72.9 |
| 9 | 1-acetyl-2-n-butoxypiperidine | 15.4 | NaBF$_4$ | 0.08 | 160 | 1-acetyl-1,2,3,4-tetrahydropyridine | 8.4 | 86.7 |
| 10 | 6-methoxypiperidone (2) | 12.9 | NaBF$_4$ | 0.11 | 160 | 3,4-dihydropyridone-(2) | 5.9 | 60.8 |
| 11 | 1-acetyl-2-methoxypiperidine | 31.4 | (CH$_3$)$_4$NBF$_4$ | 0.32 | 210 | 1-acetyl-1,2-3,4-tetrahydropyridine | 22.5 | 90.0 |
| 12 | 1-acetyl-2-methoxypi- | 31.4 | (C$_4$H$_9$)$_4$NBF$_4$ | 0.66 | 190 | 1-acetyl-1,2-3,4-tetrahy- | 22.8 | 91.1 |

Table 1-continued

Examples 2-13

| Example | Starting material (N,O-acetal) | [g] | catalyst | [g] | highest temp. in the flask [°C.] | final product (cycl.-enamide) | [g] | material yield |
|---|---|---|---|---|---|---|---|---|
| 13 | peridine 1-acetyl-2-methoxypi-peridine | 31.4 | $(C_3H_7)_4NPF_6$ | 0.66 | 160 | dropyridine 1-acetyl-1,2-3,4-tetrahy-dropyridine | 22.5 | 90.0 |

EXAMPLES 14 to 34

Anodic alkoxylation of cyclic amides and splitting off of alcohol from the alkoxyamides obtained according to the invention:

EXAMPLE 14

26.37 g of 1-formylpiperidine and 74.63 g of methanol are electrolyzed in an electrolysis cell made of glass and having a content of about 80 ml, in the presence of 0.43 g of potassium tetrafluoroborate as the supporting electrolyte. The electrodes are two concentrically arranged wire gauze platinum cylinders having 225 meshes per $cm^2$, of 15 and of 30 mm diameter and of 55 mm height, which are immerged into the solution. The outer electrode is connected so as to be the anode. During the electrolysis process, the temperature is maintained at 30° C. Upon switching on the electrolysis current, the current density in the anode is 3 A/$dm^2$. The current is switched off after a charge of 2.06 Faradays per mol of 1-formylpiperidine has passed. The calculated average cell tension is 28.0 volts. For working up purposes, the electrolysis solution is fed to a flask which is equipped with a Vigreux column and a Liebig condenser. The temperature in the flask is elevated under normal pressure to such a level that the alcohol slowly distills over. Upon reaching a temperature of from 180° to 190° C., the pressure is slowly lowered, until the reaction product, too, distills over and is collected in the receptacle.

21.2 g of 1-formyl-1,2,3,4-tetrahydropyridine (boiling point of from 109° to 112° C. under 33.8 mbars; $n_D^{25}$ 1.5222) are obtained, which corresponds to a yield of material of 81.5% and to a yield of current of 79.3%.

EXAMPLES 15 to 34

Details concerning these examples which are on principle carried out in analogous manner to Example 14 can be seen from table 2.

COMPARATIVE EXAMPLE $NH_4Br$ is the conducting salt.

33.5 g of 1-acetylpiperidine and 68.3 g of methanol are electrolyzed in an electrolysis cell analogous to that of Example 15, in the presence of 0.42 g of ammonium bromide as the supporting electrolyte. During the electrolysis process the temperature is 30° C. Upon switching on the electrolysis direct current, the current density in the anode is A/$dm^3$. After a charge of 2.1 Faradays per mol of 1-acetylpiperidine has passed, the current is switched off. The average calculated cell tension is 87.1 volts.

The electrolysis solution is worked up in analogous manner to Example 15. The temperature peak in the flask is 160° C.

19.1 g of a product ($n_D^{25}$ 1.4834), which according to the NMR spectrum consists of more than 95% of 1-acetylpiperidine (57% of originally weighed—in quantity) and contains only traces of 1-acetyl-1,2,3,4-acetylpiperidine and 13.4 g of a tarry residue, are obtained in the receptacle.

Consequently, when using ammonium bromide as the conducting salt for the preparation of 1-acetyl-1,2,3,4-tetrahydropyridine from 1-acetylpiperidine and methanol, enamide is not obtained.

Table 2:

| Example | Amine | Alcohol $R^5OH$ [g] | $R^5$ | [g] | Supporting electrolyte | [g] | Electrolysis temp. [°C.] | Current density A/$dm^2$ | Tension [V] | Current quantity F/mol |
|---|---|---|---|---|---|---|---|---|---|---|
| 15 | 1-formylpiperidine | 26.37 | $CH_3$ | 76.63 | $LiBF_4$ | 0.219 | 30 | 1.3 | 26.8 | 2.12 |
| 16 | 1-acetyl-pyrrolidine | 26.18 | $CH_3$ | 74.11 | $KBF_4$ | 0.29 | 20 | 2 | 48.8 | 2 |
| 17 | | 26.18 | | 74.11 | $NaBF_4$ | 0.25 | 20 | 2.5 | 26.4 | 2.1 |
| 18 | | 26.18 | | 74.11 | | 0.25 | 20 | 3 | 28.5 | 4.04 |
| 19 | 1-benzoyl-piperidine | 38.1 | $CH_3$ | 64.4 | $NaBF_4$ | 0.22 | 20 | 1 | 28.3 | 2.6 |
| 20 | | 38.1 | | 64.4 | $LiBF_4$ | 0.19 | 20 | 2 | 49.3 | 2.5 |
| 21 | | 38.1 | | 64.4 | $KPF_6$ | 0.37 | 20 | 3 | 36.4 | 2.4 |
| 22 | 1-acetyl-hexahydro-azepine | 31.0 | $CH_3$ | 70.3 | $NaBF_4$ | 0.24 | 20 | 2 | 23.3 | 2.2 |
| 23 | 1-acetyl-piperidine | 25.42 | $CH_3$ | 64.10 | $NaBF_4$ | 2.2 | 20 | 3.5 | 18.9 | 2.3 |
| 24 | | 25.42 | | 64.10 | | 0.7 | 20 | 3 | 28.1 | 6 |
| 25 | | 8.5 | $n-C_4H_9$ | 49.7 | | 0.9 | 20 | 0.5 | 150.2 | 2.5 |
| 26 | 1-methoxy-carbonyl-piperidine | 16.2 | $n-C_4H_9$ | 83.8 | $NaBF_4$ | 1.1 | 20 | 0.5 | 155.3 | 2 |
| 27 | | 31.32 | $CH_3$ | 70.1 | | 1.8 | 15 | 2 | 21.9 | 2.1 |
| 28 | ε-capro-lactam | 21.82 | $CH_3$ | 61.8 | $NaBF_4$ | 2.1 | 10 | 1 | 12.6 | 2.5 |

Table 2:-continued

| Example | | | | | | | | | |
|---|---|---|---|---|---|---|---|---|---|
| 29 | 1-(2'-fluoro-benzoyl)-piperidine | 40.54 | $CH_3$ | 60.7 | $NaBF_4$ | 2.15 | 50 | 3 | 15.3 | 2.5 |
| 30 | 1-(2'-chlorobenzoyl)-piperidine | 42.66 | $CH_3$ | 61.1 | $NaBF_4$ | 1.15 | 30 | 1.5 | 25.3 | 2.5 |
| 31 | 1-(3'-methyl-benzoyl)-piperidine | 40.06 | $CH_3$ | 63.15 | $NaBF_4$ | 1.25 | 30 | 1 | 46.8 | 2.5 |
| 32 | 1-benzoyl-2-methyl-piperidine | 43.83 | $CH_3$ | 60.2 | $NaBF_4$ | 1.15 | 40 | 1 | 29.3 | 2.5 |
| 33 | 1-acetyl-2-methylpiperidine | 20.66 | $CH_3$ | 59.8 | $NaBF_4$ | 0.9 | 30 | 2 | 16.6 | 2.5 |
| 34 | piperidone-(2) | 19.8 | $CH_3$ | 64.1 | $NaBF_4$ | 0.25 | 30 | 1 | 17.2 | 2.5 |

| Example | Highest temp. in the flask [°C.] | Product | [g] | Bp. [°C.] [mbar] | $n_D^{25}$ | Mp. [°C.] | Yield material [%] | Yield Current [%] |
|---|---|---|---|---|---|---|---|---|
| 15 | 137 | 1-formyl-1,2,3,4-tetrahydropyridine | 24.2 | | | | 93.4 | 88.1 |
| 16 | 160 | 1-acetyl-2-pyrroline | 17.4 | 144/130.3 | 1.5121 | | 67.8 | 67.8 |
| 17 | 150 | | 15.6 | | | | 60.7 | 57.1 |
| 18 | 150 | 1-acetylpyrrol | 13.1 | 33/0.05 | 1.5098 | | 51.9 | 51.4 |
| 19 | 160 | 1-benzoyl-1,2,3,4-tetrahydropyridine | 27.0 | 97/0.09 | 1.5839 | 33–35 | 74.1 | 57.0 |
| 20 | 140 | | 29.4 | | | | 78.1 | 62.5 |
| 21 | 140 | | 34.6 | | | | 91.9 | 76.6 |
| 22 | 170 | 1-acetyl-1-H-2,3,4,5-tetrahydroazepine | 18.8 | 34.5/0.5 | 1.5078 | | 61.7 | 56.1 |
| 23 | 130 | 1-acetyl-1,2,3,4-tetrahydropyridine | 20.62 | 67–68/4.0 | 1.5153 | | 82.4 | 71.7 |
| 24 | 150 | 1-acetyl-1,4-dihydropyridine | 16.2 | 65/0.13 | 1.5413 | | 65.7 | 43.8 |
| 25 | 160 | 1-acetyl-1,2,3,4-tetrahydropyridine | 3.8 | 67–68/4.0 | 1.5079 | | 45.1 | 36.1 |
| 26 | 160 | 1-methoxycarbonyl-1,2,3,4-tetrahydropyridine | 5.8 | 26/0.026 | 1.4904 | | 36.3 | 36.3 |
| 27 | 140 | | 22.3 | | | | 72.2 | 68.8 |
| 28 | 175 | 1-H-2,3,4,5-tetrahydroazepine-2-one | 11.5 | 110/1.33 | 1.5312 | 30 | 53.7 | 43.0 |
| 29 | 146 | 1-(2'-fluorobenzoyl)-1,2,3,4-tetrahydropyridine | 31.8 | 94/0.05 | 1.5695 | | 79.2 | 63.4 |
| 30 | 150 | 1-(2'-chlorobenzoyl)-1,2,3,4-tetrahydropyridine | 30.5 | 128/0.12 | 1.5859 | | 72.1 | 57.7 |
| 31 | 150 | 1-(3'-methylbenzoyl)-1,2,3,4-tetrahydropyridine | 29.3 | 133/0.8 | 1.5750 | | 73.9 | 59.1 |
| 32 | 145 | 1-benzoyl-2-methyl-1,2,3,4-tetrahydropyridine | 32.1 | 110–115/0.13 | 1.5507 | | 74.0 | 59.2 |
| 33 | 150 | 1-acetyl-2-methyl-1,2,3,4-tetrahydropyridine | 16.25 | 53/0.11 | 1.5098 | | 79.9 | 63.9 |
| 34 | 165 | 3,4-dihydropyridone-(2) | 8.8 | | | 31–32 | 45.3 | 36.2 |

What is claimed is:

1. A process for the preparation of a cyclic enamide of the formula

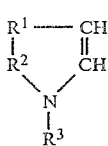

in which $R^1$ is a single bond or alkylene of from 1 to 8 carbon atoms $R^2$ is $-CH_2-CH_2-$, $-CH=CH-$,

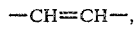

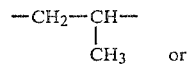

p1 in which the carbon atom carrying the $CH_3$ or the oxygen radical is bound to the ring nitrogen atom:

$R^3$ is a hydrogen atom, secondary or tertiary alkyl of 3 or 4 carbon atoms,

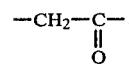

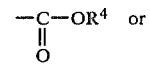

in which $R^4$ is alkyl of from 1 to 6 carbon atoms; phenyl; phenyl substituted by at least one member of the group consisting of alkyls of from 1 to 4 carbon atoms, fluorine, chlorine and bromine; benzyl; or benzyl substituted by at least one member of the group consisting of alkyls of from 1 to 4 carbon atoms, fluorine, chlorine and bromine; and $R^{4'}$ has the same meaning as $R^4$ or is hydrogen; provided that either one or the other, but not both, of the radicals $R^2$ and $R^3$ contains a

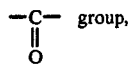 group, which comprises heating a cyclic amide of the formula

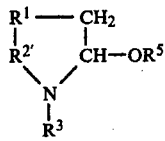

in which $R^1$ and $R^3$ are as defined previously, and $R^{2'}$ is

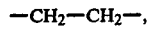

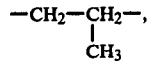

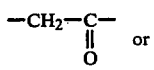

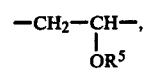

the carbon atom carrying the $CH_3$, O or $OR^5$ radical being bound to the ring nitrogen atom and $R^5$ being a primary or secondary alkyl of from 1 to 4 carbon atoms, provided that either one or the other, but not both, of the radicals $R^{2'}$ and $R^3$ contains a

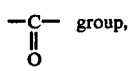 group, to a temperature of from about 100° to 250° C., in the presence of a catalyst selected from the group consisting of tetraalkylammonium salts of tetrafluoroboric acid, alkali metal salts of tetafluoroboric acid, tetraalkylammonium salts of hexafluorophosphoric acid and alkali metal salts of hexafluorophosphoric acid, and mixtures thereof, distilling off the detached alcohol $R^5OH$, and isolating the enamide.

2. A process as claimed in claim 1, which further comprises producing a cyclic amide by anodically alkoxylating a cyclic nitrogen compound of the formula

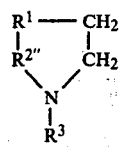

$R^1$ and $R^3$ being as defined previously and $R^{2''}$ being

—CH$_2$—CH$_2$—,

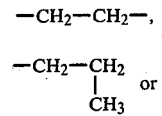

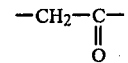

the carbon atom carrying the $CH_3$ or the oxygen radical being bound to the ring nitrogen atom, provided that either one or the other, but not both, of the radicals $R^{2''}$ and $R^3$ contains a

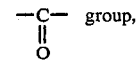 group, in an alcohol $R^5OH$, $R^5$ being as defined previously, in the presence of a supporting electrolyte which is selected from the group consisting of tetraalkylammonium salts of tetrafluoroboric acid, alkali metal salts of tetrafluoroboric acid, tetraalkylammonium salts of hexafluorophosphoric acid and alkali metal salts of hexafluorophosphoric acid, and mixtures thereof, heating the cyclic amide in the presence of a catalyst which is identical with said electrolyte, and distilling off the alcohol $R^5OH$.

3. A process for the preparation of a cyclic enamide of the formula

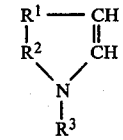

in which $R^1$ is a single bond or alkylene of from 1 to 8 carbon atoms;

$R^2$ is —CH$_2$—CH$_2$—,

—CH=CH—,

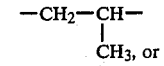

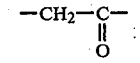

in which the carbon atom carrying the $CH_3$ or the oxygen radical is bound to the ring nitrogen atom; $R^3$ is a hydrogen atom, second or tertiary alkyl of 3 or 4 carbon atoms,

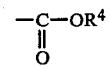

in which $R^4$ is alkyl of from 1 to 6 carbon atoms; phenyl; phenyl substituted by at least one member of the group consisting of alkyls of from 1 to 4 carbon atoms, fluorine, chlorine and bromine; benzyl; or benzyl substituted by at least one member of the group consisting of alkyls of from 1 to 4 carbon atoms, fluorine, chlorine and bromine; and $R^{4'}$ has the same meaning as $R^4$ or is hydrogen; provided that either one or the other, but not both, of the radicals $R^2$ and $R^3$ contains

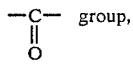 group, which consists of heating a cyclic amide of the formula

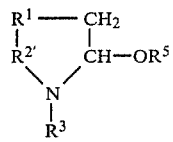

in which $R^1$ and $R^3$ are as defined previously, and $R^{2'}$ is

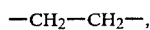

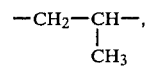

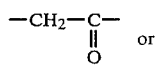

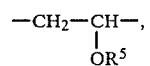

the carbon atom carrying the $CH_3$, O or $OR^5$ radical being bound to the ring nitrogen atom and $R^5$ being a primary or secondary alkyl of from 1 to 4 carbon atoms, provided that either one or the other, but not both, of the radicals $R^{2'}$ and $R^3$ contains a

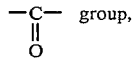 group, to a temperature of from about 100° to 250° C., in the presence of a catalyst selected from the group consisting of tetraalkylammonium salts of tetrafluoroboric acid, alkali metal salts of tetrafluoroboric acid, tetraalkylammonium salts of hexafluorophosphoric acid and alkali metal salts of hexafluorophosphoric acid, and mixtures thereof, distilling off the detached alcohol $R^5OH$, and isolating the enamide.

4. A process for the preparation of a cyclic enamide of the formula

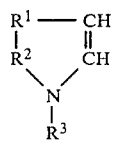

in which $R^1$ is a single bond or alkylene of from 1 to 8 carbon atoms
$R^2$ is

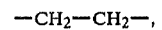

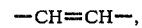

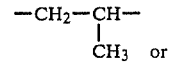

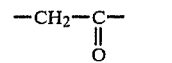

in which the carbon atom carrying the $CH_3$ or the oxygen radical is bound to the ring nitrogen atom; $R^3$ is a hydrogen atom, secondary or tertiary alkyl of 3 or 4 carbon atoms,

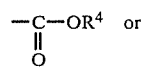 or

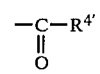

in which $R^4$ is alkyl of from 1 to 6 carbon atoms; phenyl; phenyl substituted by at least one member of the group consisting of alkyls of from 1 to 4 carbon atoms, fluorine, chlorine and bromine; benzyl; or benzyl substituted by at least one member of the group consisting of alkyls of from 1 to 4 carbon atoms, fluorine, chlorine and bromine; and $R^{4'}$ has the same meaning as $R^4$ or is hydrogen; provided that either one or the other, but not both, of the radicals $R^2$ and $R^3$ contains a

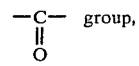 group, which consists of anodically alkoxylating a cyclic nitrogen compound of the formula

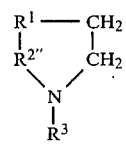

$R^1$ and $R^3$ being as defined previously and $R^{2''}$ being

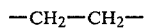

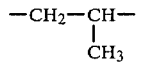

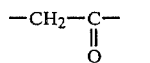

the carbon atom carrying the $CH_3$ or the oxygen radical being bound to the ring nitrogen atom; provided that either one or the other, but not both, of the radicals $R^{2''}$ and $R^3$ contains a

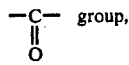 group, in an alcohol $R^5OH$, $R^5$
being as defined previously, in the presence of a supporting electrolyte which is selected from the group consisting of tetraalkylammonium salts of tetrafluoroboric acid, alkali metal salts of tetrafluoroboric acid, tetraalkylammonium salts of hexafluorophosphoric acid and alkalia metal salts of hexafluorophosphoric acid, and mixtures thereof, to produce a cyclic amide of the formula

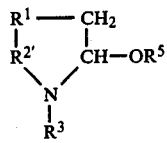

in which $R^1$ and $R^3$ are as defined previously, $R^{2'}$ is

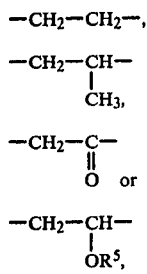

the carbon atom carrying the $CH_3$, O or $OR^5$ radical being bound to the ring nitrogen atom and $R^5$ being a primary or secondary alkyl of from 1 to 4 carbon atoms, provided that either one or the other, but not both of the radicals $R^{2'}$ and $R^3$ contains a

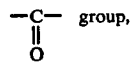 group, and heating the cyclic amide to a temperature of from about 100° to 250° C., in the presence of a catalyst which is identical with said electrolyte, distilling off the detached alcohol $R^5OH$, and isolating the enamide.

5. A process as defined in claim 1, wherein the cyclic amide is mixed with the catalyst in the presence of a solvent which is subsequently distilled off.

6. A process as claimed in claim 1, 2, or 5, wherein the cyclic amide,
if $R^{2'}$ is

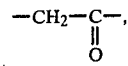

$R_1$ is branched or linear alkylene of from 1 to 8 carbonatoms and,
if $R^{2'}$ is

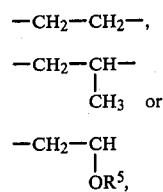

$R^1$ is a single bond or a branched or linear alkylene group of from 1 to 3 carbon atoms.

7. A process as claimed in claim 6, wherein in the cyclic amide $R^4$ is $CH_3$, $C_2H_5$, $C_6H_5$, $C_6H_5CH_2$, substituted $C_6H_5$ or substituted $C_6H_5CH_2$ and $R^{4'}$ is $CH_3$, $C_2H_5$, $C_6H_5$, $C_6H_5CH_2$, substituted $C_6N_5$, substituted $C_6H_5CH_2$ or H and $R^5$ is $CH_3$.

8. A process as claimed in claim 7 wherein the catalyst is sodium tetrafluoroborate, potassium tetrafluoroborate, sodium hexafluorophosphate, potassium hexafluorophosphate, or a mixture thereof.

9. A process as claimed inn claim 8, wherein the catalyst is present in an amount of from about 0.1 to 20% by weight, calculated on the cyclic amide.

10. A process as claimed in claim 9, wherein the cyclic amide is heated in the presence of the catalyst to a temperature of from about 120° to 180° C.

11. A process as claimed in claim 10, wherein the cyclic amide is heated at reduced pressure.

12. A process as claimed in claim 11, wherein $R^4$ and $R^{4'}$ are phenyl or benzyl is substituted by 1 or 2 of said members.

13. A process as claimed in claim 1, 2 or 5 wherein in the cyclic amide $R^4$ is $CH_3$, $C_2H_5$, $C_6H_5$, $C_6H_5CH_2$, substituted $C_6H_5$ or substituted $C_6H_5CH_2$ and $R^{4'}$ is $CH_3$, $C_2H_5$, $C_6H_5$, $C_6H_5CH_2$, substituted $C_6H_5$, substituted $C_6H_5CH_2$ or H and $R^5$ is $CH_3$.

14. A process as claimed in claim 1, 2 or 5 wherein the catalyst is sodium tetrafluoroborate, potassium tetrafluoroborate, sodium hexafluorophosphate, potassium hexafluorolphosphate, or a mixture thereof.

15. A process as claimed in claim 1, 2 or 5, wherein the catalyst is present in an amount of from about 0.1 to 20% by weight, calculated on the cyclic amide.

16. A process as claimed in claim 1, 2 or 5 wherein the cyclic amide is heated in the presence of the catalyst to a temperature of from about 120° to 180° C.

17. A process as claimed in claim 1, 2 or 5 wherein the cyclic amide is heated at reduced pressure.

18. A process as defined in claim 1, 2 or 5 wherein $R^4$ and $R^{4'}$ are phenyl or benzyl substituted by 1 or 2 of said members.

* * * * *